United States Patent
Armijo

(10) Patent No.: US 6,719,135 B2
(45) Date of Patent: Apr. 13, 2004

(54) CATHETER PACKAGING DEVICE

(75) Inventor: Brian O. Armijo, Mountain View, CA (US)

(73) Assignee: SciMed Lifesystems, Inc., Maple Grove, MN (US)

(*) Notice: Subject to any disclaimer, the term of this patent is extended or adjusted under 35 U.S.C. 154(b) by 82 days.

(21) Appl. No.: 10/028,042

(22) Filed: Dec. 21, 2001

(65) Prior Publication Data

US 2002/0130059 A1 Sep. 19, 2002

Related U.S. Application Data

(60) Provisional application No. 60/276,795, filed on Mar. 16, 2001.

(51) Int. Cl.$^7$ ............................................. B65D 83/10
(52) U.S. Cl. ........................................ 206/364; 206/438
(58) Field of Search ................................ 206/363–366, 206/438, 63.3, 303, 564, 388, 389, 565

(56) References Cited

U.S. PATENT DOCUMENTS

| | | | |
|---|---|---|---|
| 3,633,758 A | | 1/1972 | Morse et al. |
| 4,216,860 A | * | 8/1980 | Heimann .................... 206/370 |
| 4,713,059 A | | 12/1987 | Bickelhaupt et al. |
| 4,779,727 A | | 10/1988 | Taterka et al. |
| 5,344,011 A | | 9/1994 | DiBernardo et al. |
| 5,372,254 A | | 12/1994 | Gross |
| 5,392,918 A | * | 2/1995 | Harrison .................... 206/571 |
| 5,568,865 A | | 10/1996 | Mase et al. |
| 5,738,213 A | * | 4/1998 | Whiting et al. ............. 206/364 |
| 5,769,222 A | * | 6/1998 | Banerian .................... 206/364 |
| 5,848,691 A | | 12/1998 | Morris et al. |
| 5,947,284 A | * | 9/1999 | Foster ........................ 206/364 |
| 6,047,825 A | | 4/2000 | Samuels |
| 6,053,313 A | | 4/2000 | Farrell et al. |
| 6,068,121 A | | 5/2000 | McGlinch |

FOREIGN PATENT DOCUMENTS

| | | |
|---|---|---|
| EP | 0 782 868 | 7/1997 |
| EP | 0 820 781 | 1/1998 |

\* cited by examiner

Primary Examiner—Shian Luong
(74) Attorney, Agent, or Firm—Crompton, Seager & Tufte, LLC

(57) ABSTRACT

A holder for holding and retaining a catheter during storage, shipping, and prior to use in a patient is described. The holder includes a first member and a second member attached to a central hub, the first and second members designed and configured to releasably retain the distal and proximal ends of the catheter. Also attached to the central hub is a plurality of retaining members for receiving and retaining the elongate catheter body in a coiled configuration.

6 Claims, 9 Drawing Sheets

CATHETER PACKAGING DEVICE

CROSS-REFERENCE TO RELATED APPLICATIONS

This application claims benefit under 35 U.S.C. §119 of U.S. Provisional Patent Application No. 60/276,795, filed Mar. 16, 2001.

FIELD OF THE INVENTION

The present invention relates to a catheter packaging device for use particularly, but not exclusively, with a percutaneous translumenal coronary angioplasty catheter (PTCA).

BACKGROUND OF THE INVENTION

Catheters are tubular medical devices for insertion into canals, vessels, passageways, or body cavities in order to inject or withdraw fluid or, in the case of balloon catheters, to open a lumen. While catheters vary in size, shape, and function, they frequently consist of a very long, flexible, and thin tubular portion connected at their proximal end, e.g., the end of the catheter not contained within the patient's body during use, to a fitting or accessory of some kind. For example, PTCA or balloon catheters may have a luer fitting at the proximal end. The distal end of the catheter, e.g., the end of the catheter inserted into the patient's body during use, often caries a medical accessory, such as a balloon or a stent.

The tubular portion of the catheter may be a meter or longer in length, and only a fraction of an inch in diameter. The tubular portion of the catheter is usually hollow, and may have one or more lumens running along its entire length. The lumen or lumens function as a way of inserting various devices into the catheter. For example, catheters frequently travel along a guidewire running through one of the lumens. Alternatively, the lumens may receive mechanical devices and control wires for removing clots within blood vessels, for assisting in surgical operations, for retrieving tissue samples, etc.

Due to the extremely fine and often delicate nature of the lumens, as well as the slight tolerances associated with many of the applications to which catheters are applied, catheters must necessarily be handled, stored, and shipped with great care. Mechanical or chemical abrasion to any portion of the exterior of the catheter can cause problems to the subsequent use of the catheter. Also, "kinking" or deformation of the catheter body will render the device unsuitable for use. Deformation should also be avoided while installing or removing a catheter from a storage or shipping packaging device.

Thus, a need exists for a catheter holder that securely retains a catheter, and in particular a catheter having delicate accessories at its distal end, during storage, shipping, and prior to use in a patient.

SUMMARY OF THE INVENTION

A holder for retaining a catheter is disclosed which comprise a central hub, and attached to the hub, a first member attached to the hub having (i) an end stop, (ii) a recessed channel configured to receive a catheter's distal end region; and (iii) a recessed pocket member configured to receive an accessory disposed in the catheter's distal end region. A second member, also attached to the hub, is configured to releasably retain a catheter proximal end accessory. The holder also include a plurality of retaining members attached to the hub. The retaining members are configured to receive and retain an elongate catheter body.

These and other objects and features of the invention will be more fully appreciated when the following detailed description of the invention is read in conjunction with the accompanying drawings.

BRIEF DESCRIPTION OF THE DRAWINGS

FIG. 3B shows a catheter positioned in the holder for transit and/or storage;

DETAILED DESCRIPTION OF THE PREFERRED EMBODIMENTS

Figure 1:
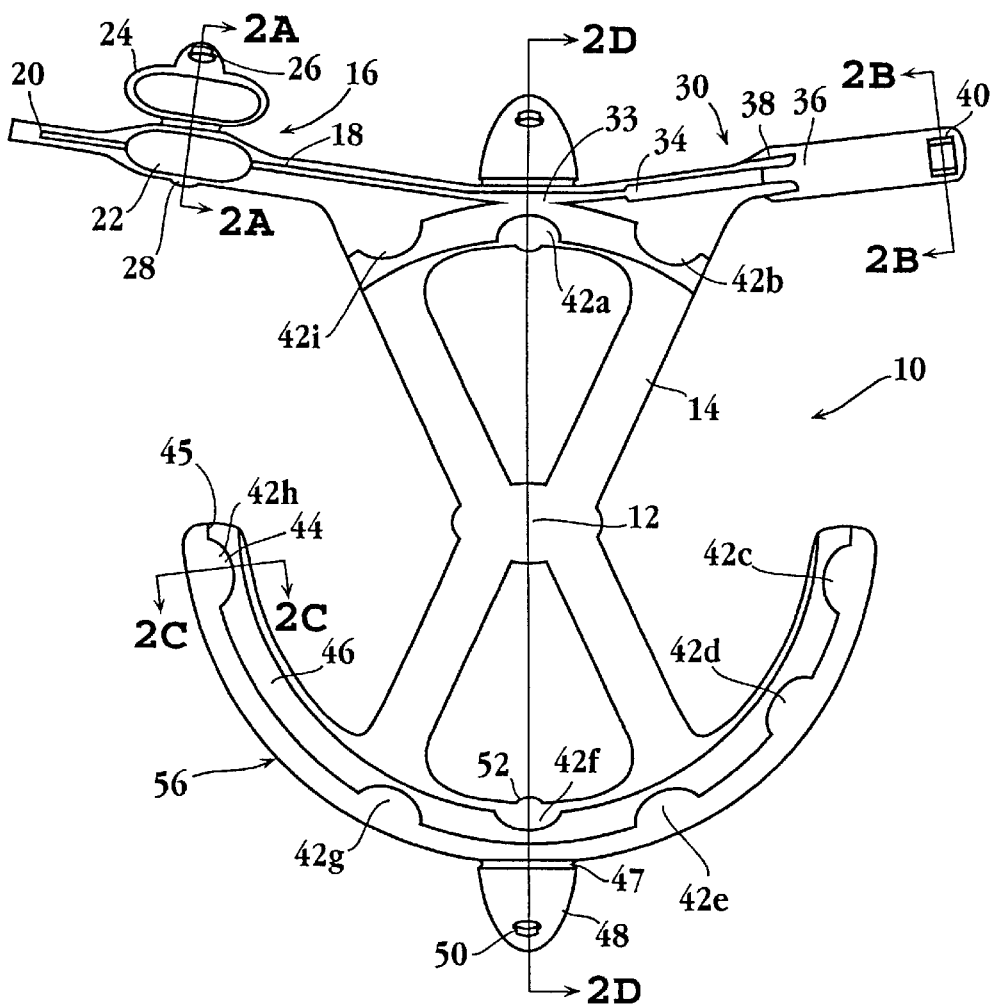
FIG. 1 is a plan view of one embodiment of the catheter holder according to the invention.

The present invention relates to a holder suitable for retaining a catheter during storage, shipping, and prior to use. Referring now to the Figures, in which like numerals identify like features, FIG. 1 is a top plan view of an embodiment of a catheter holder, generally designated as 10, constructed in accordance with the present invention. The holder includes a central hub 12 for support and/or attachment of various holder members. The central hub is not necessarily disposed in the actual center of the holder, as will be apparent from the holder embodiment to be described with respect to FIG. 4A. Emanating from the central hub is at least one arm, such as arm 14. The holder embodiment shown in FIG. 1 has four arms, however, it will be appreciated that fewer or more arms would be suitable and are contemplated.

Joined to central hub 12 is a first member 16 designed and configured for receiving and retaining the distal end, and any accompanying accessories, of a catheter. The first member includes a recessed groove or channel 18 dimensioned to receive the catheter's distal end. Channel 18 terminates at the tip of the first member to form an end stop 20 against which the distal tip of the catheter, typically a guide wire or needle, abuts, as seen best in FIG. 3B. The end stop serves to secure the catheter during placement in the device and, after placement in the holder, to prevent slippage of the catheter from the holder.

Figure 2A:
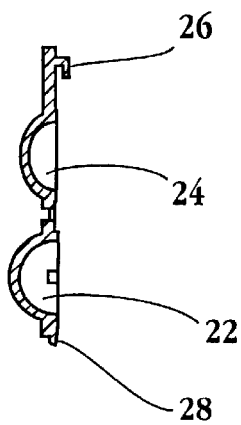
FIGS. 2A–2D are sectional views along lines A—A, B—B, C—C, and D—D respectively of FIG. 1.

First member 16 also includes a pocket 22 dimensioned for placement of a catheter accessory, such as a balloon and/or an endovascular stent. In the embodiment shown in FIG. 1, a hinged cover 24 is movable between an open position, as shown in FIG. 1, and a closed position (not shown). A slip lock 26 or other similar mechanism fastens the cover against opposing lip 28 to releasably secure the cover in its closed position. Together, the pocket and the hinged cover in its closed position protect the catheter accessories during storage and transit. It will be appreciated that the hinged cover is an optional feature, since an accessory resting in the pocket lies below the planar surface of the holder and is adequately protected during storage and transit. A sectional view of pocket 22 is shown in FIG. 2A.

Figure 2B:
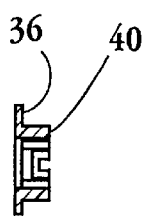
Figure 3A:
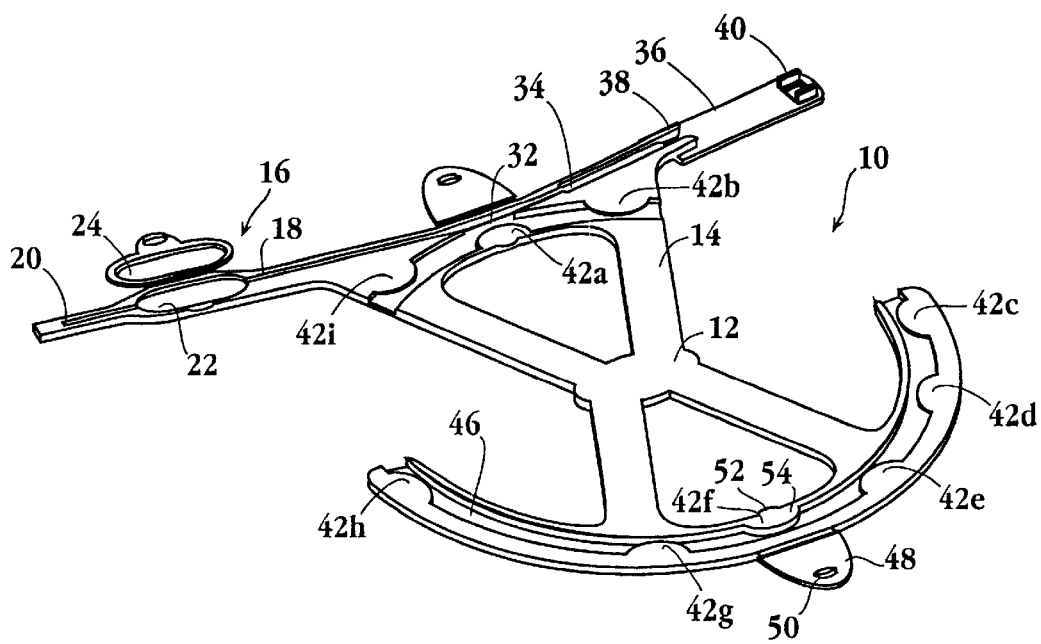
FIGS. 3A–3B are perspective views of the catheter holder in FIG. 1, where

Also attached to central hub 12 is a second member designed and configured for receiving and retaining the proximal end, and any accompanying accessories, of a catheter. Recessed channel 18 continues across a point of intersection 32 and then increases in depth and width to form a wider channel, as seen in FIGS. 1 and 3 at 34, to accommodate the catheter's distal end accessory. Channel 34 opens onto a base plate 36 dimensioned to retain an end accessory, such as a luer lock. A step or change in profile 38 is present at the junction between channel 34 and base plate 36. The step is sized such that the top surface of a proximal end accessory when placed in the second member lies in the plane of the central hub of the holder. That is, the step at junction 38 is approximately the diameter of the end accessory. Thus, the base plate is offset from the plane of the central hub by the diameter of the end accessory. The base plate terminates in a mechanism to releasably secure the end accessory to the base plate. Suitable mechanisms include prongs for a snap fit, as shown at 40 in FIGS. 1 and 3 and in sectional view in FIG. 2B, or a hinged clasp or hook or other suitable retainer known to those of skill.

Figure 2C:
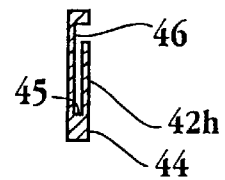
Figure 2D:
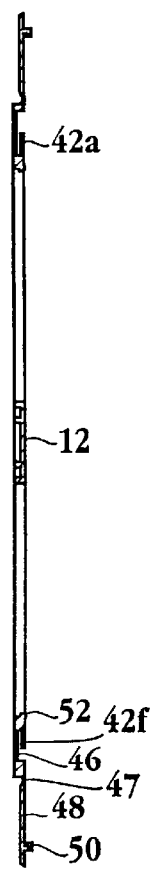
Figure 3B:
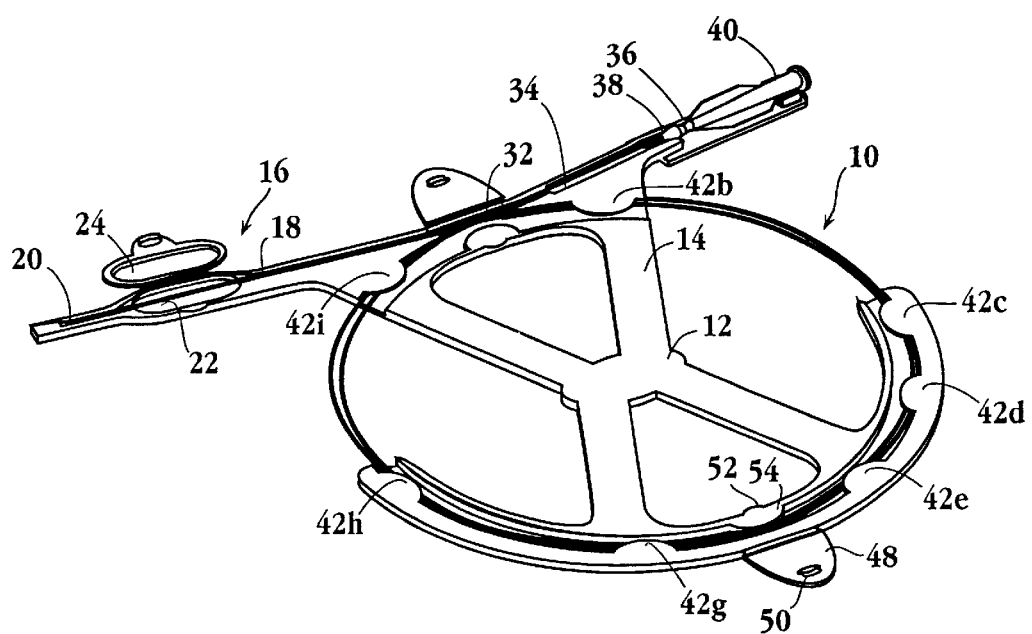

Also attached to the central hub 12 is a plurality of retaining members, such as retaining members 42a–42i, in FIG. 1. The retaining members 42a–42i are preferably oriented to retain a catheter in a coiled configuration, however, it will be appreciated that the retaining members and the first and second members could be arranged to retain the catheter in an elongate configuration, a "U" configuration, or other configuration. The retaining members can be passive, such as retaining members 42b–e, or active, such as members 42a and 42f. The passive retaining members are comprised of an upper lip, such as lip 44 on member 42h. Lip 44 extends inwardly in the direction of the central hub and over a recessed groove 46 dimensioned to retain the catheter elongate tubular body. As seen in the sectional view in FIG. 2C, a back wall 45 joins the lip and the groove and provides a structure against which the coils of the catheter tubular body press when placed in the holder, as shown in FIG. 3B. While not required, some of the retaining members can be active by configuring the upper lip to include a hinge 47 for movement between an open position, as shown in FIG. 1 for member 42f, and a closed position in which the inwardly (in the direction of the central hub) moveable lip 48 encloses groove 46 where the catheter body is retained. A releasable locking mechanism can be provided to secure the lip in its closed position. A variety of releasable locking mechanisms are known and are suitable. A snap closure is illustrated in FIG. 1 where a prong 50 is provided on moveable lip 48 for locking against an opposing fixture 52. The active retaining members can also include a projection 54 into grove 46 that functions to guide the catheter body into place against back wall 45.

Another optional active retaining member 42a is positioned at point of intersection 32, described above. As seen best in FIG. 3B, at the point of intersection, the distal portion of the catheter retained in first member 16, the proximal portion of the catheter retained in second member 30, and one or more coils of elongate catheter body overlap and intersect. Retaining member 42a, like retaining member 42f described above, is a means for actively retaining these intersection catheter portions at this point of intersection.

The retaining members in FIG. 1 are connected by a base member 56 to form curved body 58. In an alternative embodiment, retaining members remain unconnected by a base member, as shown in the embodiment illustrated in FIG. 4B.

Figure 4A:
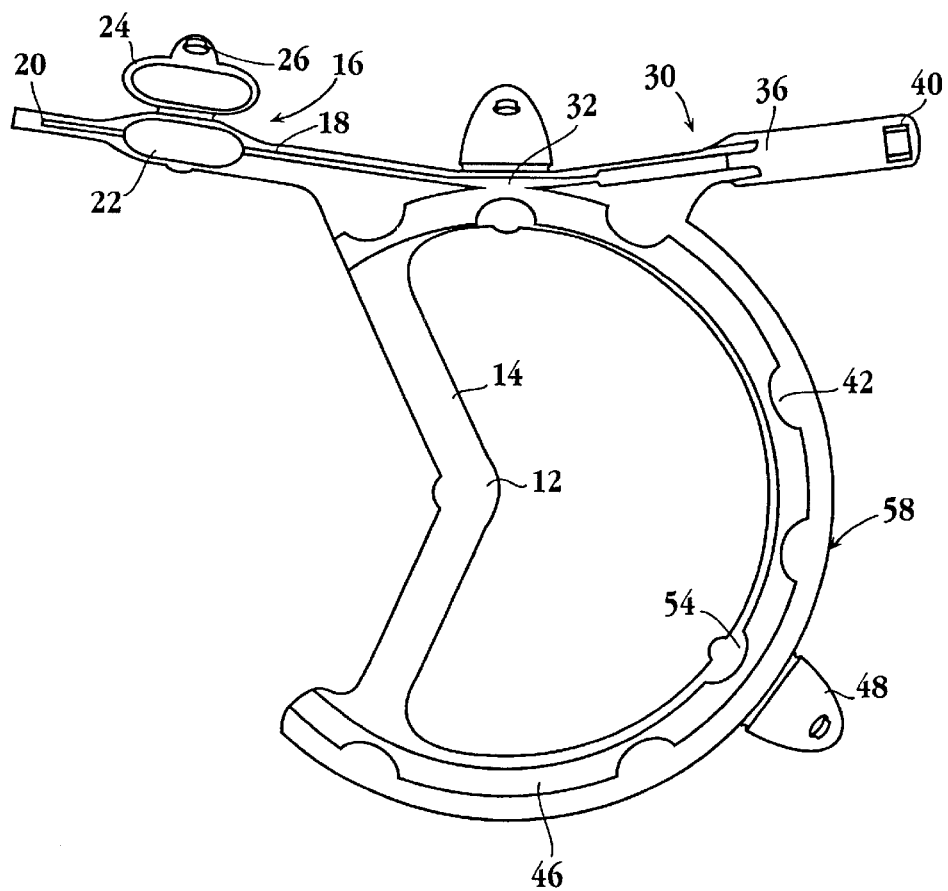
FIGS. 4A–4C are plan views of alternative embodiments of the catheter holder of the invention.
Figure 4B:
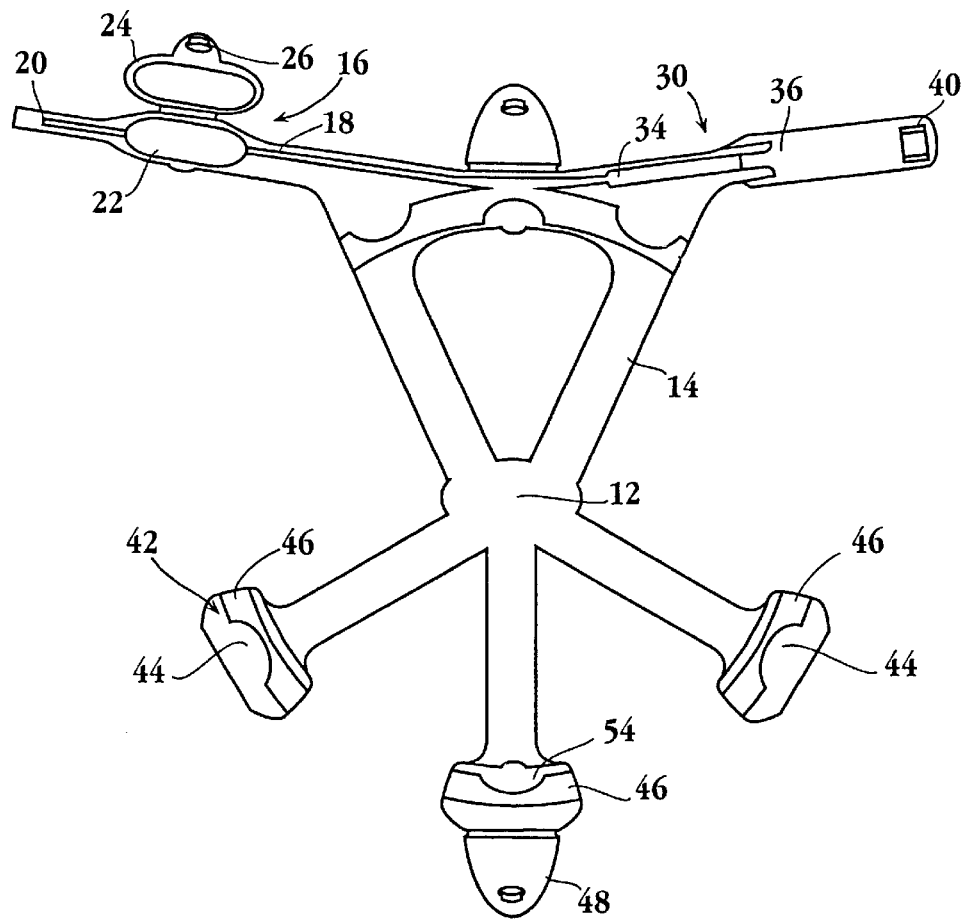
Figure 4C:
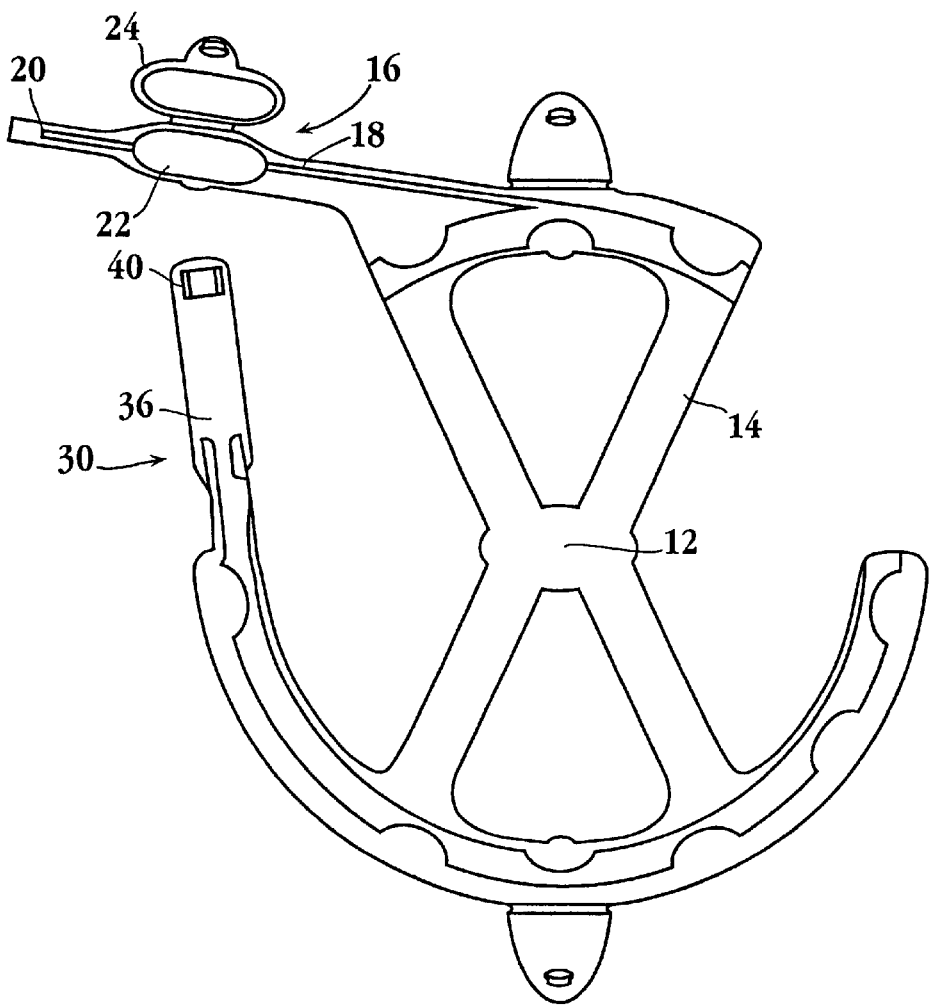

FIGS. 4A–4C illustrate other embodiments of the holder, where like features are identified by like numerals. In FIG. 4A, the curved body 58 connecting the retaining members, such as member 42, is contiguous with the first and second members, 16, 30, respectively. In the embodiment of FIG. 4B, as noted above, the retaining members lie at the distal end of arms joined to the central hub. The members are not connected by a common base member. FIG. 4C illustrates an alternative placement for the second member that retains the catheter's proximal accessories.

Figure 5A:
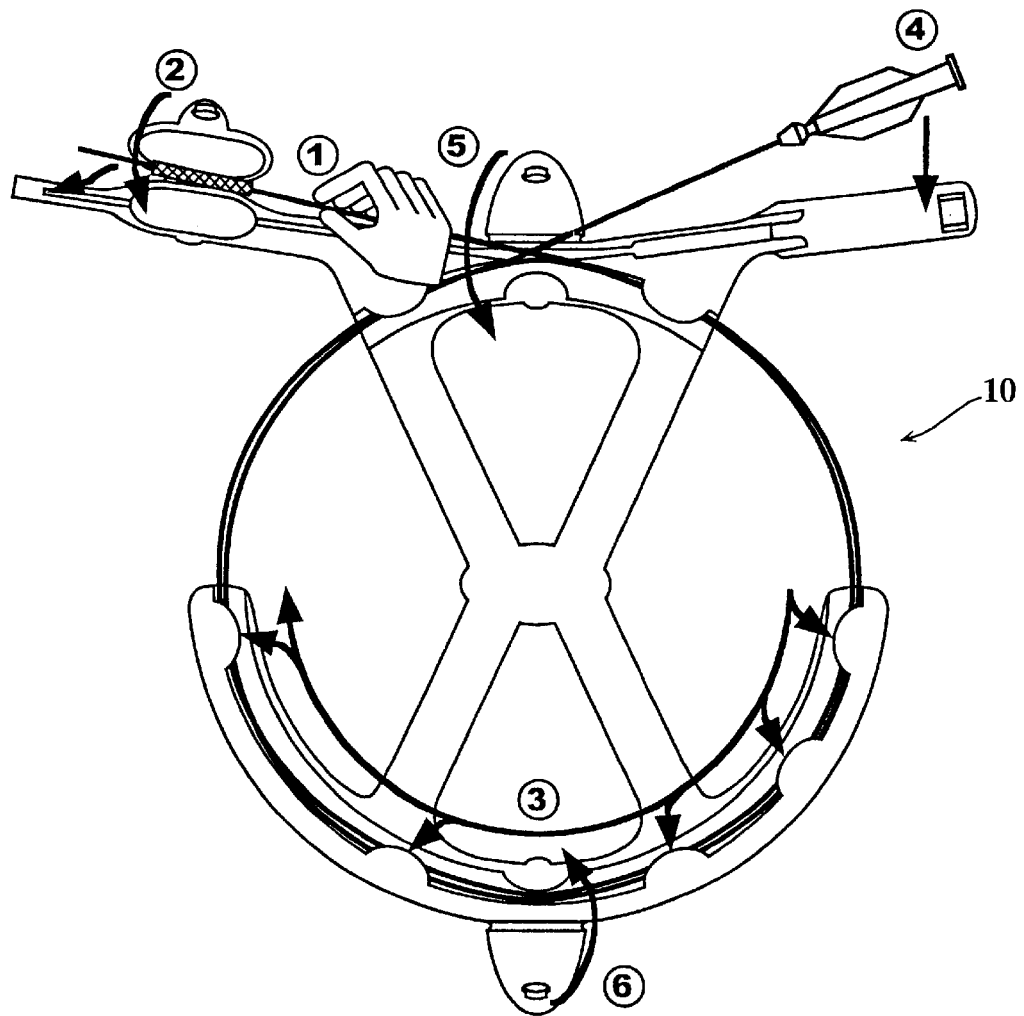
FIG. 5A illustrates a stepwise procedure for placing a catheter into the holder.

FIG. 5A illustrated the sequence of steps to place a catheter in the holder for storage and/or transit. First, the distal end of the catheter is placed into the channel of the first member (step 1 in FIG. 5A). The distal tip abuts the end stop, fixing the distal end in place. If the holder includes the optional hinged cover over the pocket, the cover is closed over any external accessory mounted on the catheter (step 2 in FIG. 5A). The elongate body of the catheter is then coiled into the groove of each retaining member, the coil resting under the upper lip of each retaining member and pressing against the wall disposed between the groove and the upper lip of each retaining member (step 3 in FIG. 5A). Depending on the length of the catheter, one or more coils of elongate catheter body are placed within each retaining member. After coiling the elongate catheter body into the retaining members, the proximal end of the catheter is secured in the second member (step 4 in FIG. 5A). Then, any active retaining members are placed in their closed positions (steps 5 and 6 in FIG. 5A). The catheter and holder can then be sterilized and further packaged as desired for storage and transport.

Figure 5B:
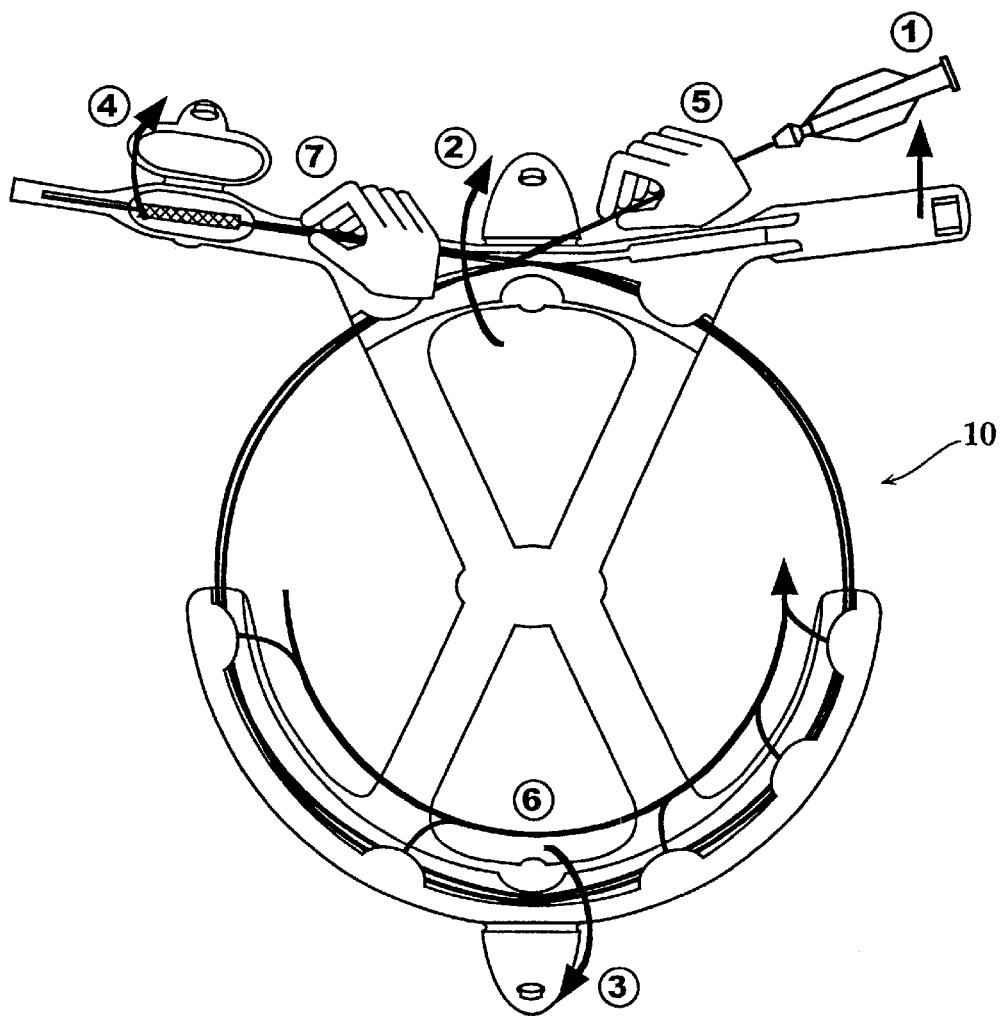
FIG. 5B illustrates a stepwise procedure for removing a catheter from the holder.

FIG. 5B illustrates the sequence of steps to remove a catheter from the holder. First, the proximal end of the catheter is released from the holder. Then any active retaining members are released, as illustrated in steps 2 and 3 of FIG. 5. Similarly, if the holder includes a hinged cover over the pocket in which the distal end accessory is stored, the cover is opened, as shown in step 4. The proximal end of the catheter is removed from the holder, followed by the coils of elongate body, and then the distal end is removed (steps 5, 6, and 7 of FIG. 5).

Any material with sufficient rigidity to support the catheter and to handle is suitable.

From the foregoing, it can be seen how various objects and features of the invention are met. The holder described herein provides a compact and efficient storage means for a catheter. In particular, the holder provides for protection of an accessory carried on the distal end of the catheter, since such an accessory is retained and protected in the pocket of the first member. As can be appreciated, the holder readily accommodates catheters of various dimensions, since the recessed grooves in the first and second members and in the retaining members can be sized as needed for catheters of various gauges. Moreover, catheters of various lengths are readily accommodated by adjusting the number of coils or by adjusting the dimensions i.e., the length of the arms emanating from the central hub, of the holder. Importantly, a catheter stored in the holder is easily removed and, upon removal, is in the correct presentation for use in a patient. That is, the proximal end is held in one hand, with the catheter body coiled and secured in the other hand, along with the distal tip.

Although the invention has been described with respect to particular embodiments, it will be apparent to those skilled in the art that various changes and modifications can be made without departing from the invention.

What is claimed is:

1. A holder for retaining a catheter, comprising: a central hub; a first member attached to the hub, said first member having (i) an end stop, (ii) a recessed channel configured to receive a catheter's distal end region; and (iii) a recessed pocket member configured to receive an accessory disposed in the catheter's distal end region; a second member attached to the hub and configured to releasably retain a catheter proximal end accessory; and a plurality of retaining members attached to the hub, said retaining members configured to receive and retain an elongate catheter body wherein at least one retaining member from said plurality of retaining members comprises a recessed channel for receiving the catheter body and a lip movably mounted for movement between an open position and a closed position toward and away from said recessed channel.

2. A holder for retaining a catheter, comprising: a central hub; a first member attached to the hub, said first member having (i) an end stop, (ii) a recessed channel configured to receive a catheter's distal end region; and (iii) a recessed pocket member configured to receive an accessory disposed in the catheter's distal end region; a second member attached to the hub and configured to releasably retain a catheter proximal end accessory: and a plurality of retaining members attached to the hub, said retaining members configured to receive and retain an elongate catheter body wherein said pocket member further comprises a cover movably mounted for movement between an open and a closed position toward and away from said pocket member.

3. A holder for retaining a catheter, comprising: a central hub lying in a plane; a first member attached to the hub, said first member having (i) an end stop, (ii) a recessed channel configured to receive a catheter's distal end region; and (iii) a recessed pocket member configured to receive an accessory disposed in the catheter's distal end region a second member attached to the hub and configured to releasably retain a catheter proximal end accessory having a diameter; and a plurality of retaining members attached to the hub, said retaining members configured to receive and retain an elongate catheter body wherein said second member is dimensioned to releasably retain a proximal end accessory in a releasable fixture mounted on a base plate, said base plate offset from the plane in which the central hub lies by the diameter of the proximal end accessory.

4. The holder of claim 3, wherein said second member releasably retains a catheter proximal and accessory by means of a snap fitting.

5. A holder for retaining a catheter, comprising: a central hub; a first member attached to the hub, said first member having (i) an end stop, (ii) a recessed channel configured to receive a catheter's distal end region; and (iii) a recessed pocket member configured to receive an accessory disposed in the catheter's distal end region; a second member attached to the hub and configured to releasably retain a catheter proximal end accessory; and a plurality of retaining members attached to the hub, said retaining members configured to receive and retain an elongate catheter body wherein said first member and said second member are oriented such that a catheter when placed in said holder overlaps on itself at a point of intersection between the recessed channel in the first member and a recessed channel in the second member, said holder further comprising a retaining member disposed at said point of intersection, said retaining member having a movable lip for movement between an open and a closed position over said recessed channel.

6. A holder for retaining a catheter, comprising: a central hub; a first member attached to and radially extending from the hub, said first member having (i) an end stop, (ii) a recessed channel configured to receive a catheter's distal end region; and (iii) a recessed pocket member configured to receive an accessory disposed in the catheter's distal end region; a second member attached to and radially extending from the hub and configured to releasably retain a catheter proximal end accessory; and a plurality of retaining members attached to the hub, said retaining members configured to receive and retain an elongate catheter body.

* * * * *

UNITED STATES PATENT AND TRADEMARK OFFICE
CERTIFICATE OF CORRECTION

PATENT NO. : 6,719,135 B2
DATED : April 13, 2004
INVENTOR(S) : Armijo

It is certified that error appears in the above-identified patent and that said Letters Patent is hereby corrected as shown below:

Column 5,
Line 26, after "body" and before "wherein", insert -- , --.
Line 35, after "region" and before "a second", insert -- ; --.

Column 6,
Lines 1 and 18, after "body" and before "wherein", insert -- , --.

Signed and Sealed this

Thirty-first Day of August, 2004

JON W. DUDAS
*Director of the United States Patent and Trademark Office*